United States Patent [19]

Bills et al.

[11] Patent Number: 5,304,485
[45] Date of Patent: Apr. 19, 1994

[54] ANTIBIOTIC PRODUCING MICROORGANISM

[75] Inventors: Gerald F. Bills, Cranford, N.J.; Fernando Pelaez, Madrid, Spain

[73] Assignee: Merck & Co., Inc., Rahway, N.J.

[21] Appl. No.: 962,548

[22] Filed: Oct. 19, 1992

[51] Int. Cl.$^5$ ............................ C12N 1/14; C12P 7/26
[52] U.S. Cl. ................................. 435/254.1; 435/148
[58] Field of Search .................................. 435/148, 254

[56] References Cited

PUBLICATIONS

Weber et al, Tetrahedron Letters, 33(9):1157–60, (1992).
ATCC Fungi/Yeasts, p. 366, 17th edition, 1987.
Ahmed, S. I. et al, Revision of Sporormia and Sporormiella, Can. J. Bot., 50, pp. 419–477 (1972).
Ellis, M. B. et al, Microfungi on Miscellaneous Substrates, pp. 140–143, Timber Press, (1988) Portland, Oreg.

*Primary Examiner*—Douglas W. Robinson
*Assistant Examiner*—Maria L. Osoteo
*Attorney, Agent, or Firm*—Richard C. Billups; Mark R. Daniel; Joseph F. DiPrima

[57] ABSTRACT

An organism of the Sporormiella species produces a compound having the formula

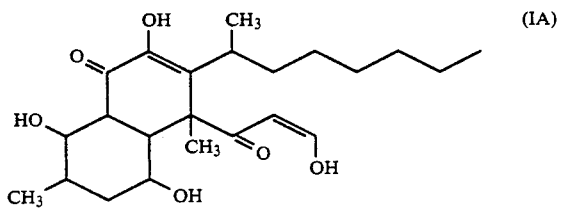

which is useful. The compound is useful as an antifungal agent.

2 Claims, 3 Drawing Sheets

ANTIBIOTIC PRODUCING MICROORGANISM

DISCLOSURE OF THE INVENTION

It has now been discovered that a novel microorganism isolated from the dung of moose produces on aerobic fermentation of a suitable nutrient medium, a compound represented by the formula

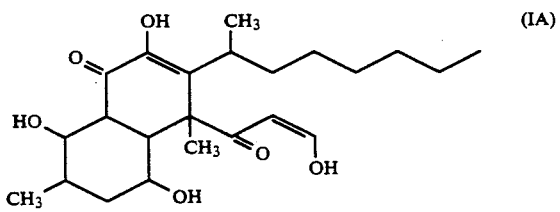

The compound which is especially effective as an antifungal agent is the subject of concurrently filed copending application, Ser. No. 07/963,178, filed Oct. 19, 1992. It is also an intermediate for acetate derivatives which have antimicrobial properties.

The present invention also embraces using the organism to produce the antifungal agent. The compound produced by the organism is also useful for preparing compounds which also have antimicrobial properties and which may be represented by the formula

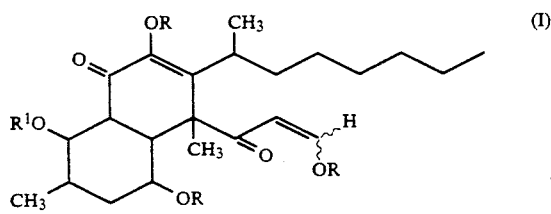

When R is $-COCH_3$ and $R^1$ is H (Compound IB) or R and R' are $-COCH_3$ (Compound IC), the compounds may be prepared by the reaction of Compound IA with an appropriate acetylating agent as hereinafter more fully described.

DETAILED DESCRIPTION OF THE INVENTION

Isolation of *Sporormiella australis*

The producing organism of the present invention was isolated from a sample of moose dung collected in northern Minnesota. To isolate the organism, a sample of moose dung was first thoroughly washed with tap water. About 0.75 gram of the sample was then homogenized in a blender and resuspended in 150 milliliters of sterile distilled water. A 1:10 dilution was made from this suspension, and different volumes (0.1 to 0.5 ml) of both the dilution and the initial suspension were plated onto DPY (dextrose-peptone-yeast extract) plates. DPY medium was of the following composition (per liter):

| Component | Amount |
| --- | --- |
| Dextrose | 5.0 g |
| Peptone | 1.0 g |
| Yeast extract | 2.0 g |
| NH4OH | 1.0 g |
| K2H2PO4 | 1.0 g |
| MgSO4.7H2O | 0.5 g |
| FeCl3.6H2O | 0.5 ml of 1% soln. |
| oxgall (dried bovine bile) | 5.0 g |

Plates were incubated at 24° C. for 3–7 days, and the growing colonies were transferred to Potato Dextrose Agar (Difco) plates. After incubating the new plates for one week at 24° C., all the cultures isolated from the sample were morphologically compared. Strains were selected for fermentation studies. One of the strains was subsequently designated MF5672 and was used in the fermentation which produced Compound IA.

*Sporormiella australis* MF 5672, the microorganism of the present invention, is in the culture collection of Merck & Co., Rahway, N.J. and has been deposited under the Budapest Treaty in the culture collection of the American Type Culture Collection at 12301 Parklawn Drive, Rockville, Md. 20852, and assigned accession number, ATCC. 74157.

The microorganism of the present invention is a fungus which was isolated from moose dung (*Alces alces*) collected in Minnesota and identified as *Sporormiella australis* (Ascomycotina, Pleosporales) *Sporormiella australis* has colonial and morphological properties as follows:

Colonies on oatmeal agar (Difco) at 20° C., 95% relative humidity, 12 hour photoperiod under fluorescent light, attaining 34–37 mm in 14 days, appressed to felty of sparsely floccose at the center, with margin even and submerged, dry, dull, pale gray to dark olivaceous gray, Pale Smoke Gray, Deep Grayish Olive, Iron Gray, Dark Olive-Black (capitalized color names from Ridgway, R. 1912. *Color Standards and Nomenclature*, Washington, D.C.), often developing conspicuous lightly pigmented sectors that originate from inoculum source, with sectors pale olivaceous yellow to pinkish olive, Avellaneous, Deep Olive Buff, reverse dull olivaceous gray to gray, pinkish gray or yellow in the sectors, Exudates and odors absent.

Colonies on malt extract agar (Difco), same conditions, attaining 26–28 mm in 14 days, appressed to felty, becoming sparsely floccose, dry, dull, with margin even, submerged, white, pale gray to dull olivaceous gray, Pale Smoke Gray, Smoke Gray, Grayish Olive, developing unpigmented sectors, reverse dark gray to nearly black, with yellow to grayish sectors. Exudates and odors absent.

Colonies on cornmeal agar (Difco), same conditions, attaining 8–12 mm in 14 days, similar in color and appearance to colonies on male yeast extract agar, but more translucent.

Colonies of this strain, as well as those of other Sporomiella spp., have a strong tendency to develop aberrant and attenuated sectors, especially after repeated transfer. These sectors are generally paler in color and have lost or have reduced their ability to differentiate stromata and/or pseudothecia.

Ascoma a pseudothecium. Pseudothecia evident in 10–21 days, maturing in 4–5 weeks on oatmeal agar. Pseudothecia single to densely gregarious, or confluent, embedded, with upper 10–60% protruding above the surface, 100–400 μm in diameter, globose to subglobose, with a minute apical papilla, non-ostiolate, glabrous, dull, black. In culture, pseudothecia often become moribund and fail to fully mature with 4–8 weeks. Often development is arrested with only the formation of asci initials and paraphyses. Peridium thin, 1–3 cells thick, a textura angularis. Peridial cells isodiametric, 3–8 μm in diameter, gray to dark olivaceous grey in KOH. Asci abundant, arising from the base of the psuedothecial cavity, bitunicate, 8-spored, cylindrical, straight to slightly curved, with broad rounded apex, 110–160×15–21 μm, tapering abruptly at the base into a short stalk, with basal stalk 5–10 μm long. Paraphyses abundant, interspersed among asci, filamentous, 1–3 μm wide, septate, approximately equal in length with asci. Ascospores biseriate within the ascus, 32–42×6–9 μm, 4-celled, constricted at the septa, with terminal cells with rounded apices, central cells cylindrical to doliform, each cell with an thin, faint lateral germ slit, with entire ascospore surrounded by a thin, refractive, hyaline sheath, with cells often separating when removed from ascus, dark olivaceous or brownish gray in KOH.

Figure 1:
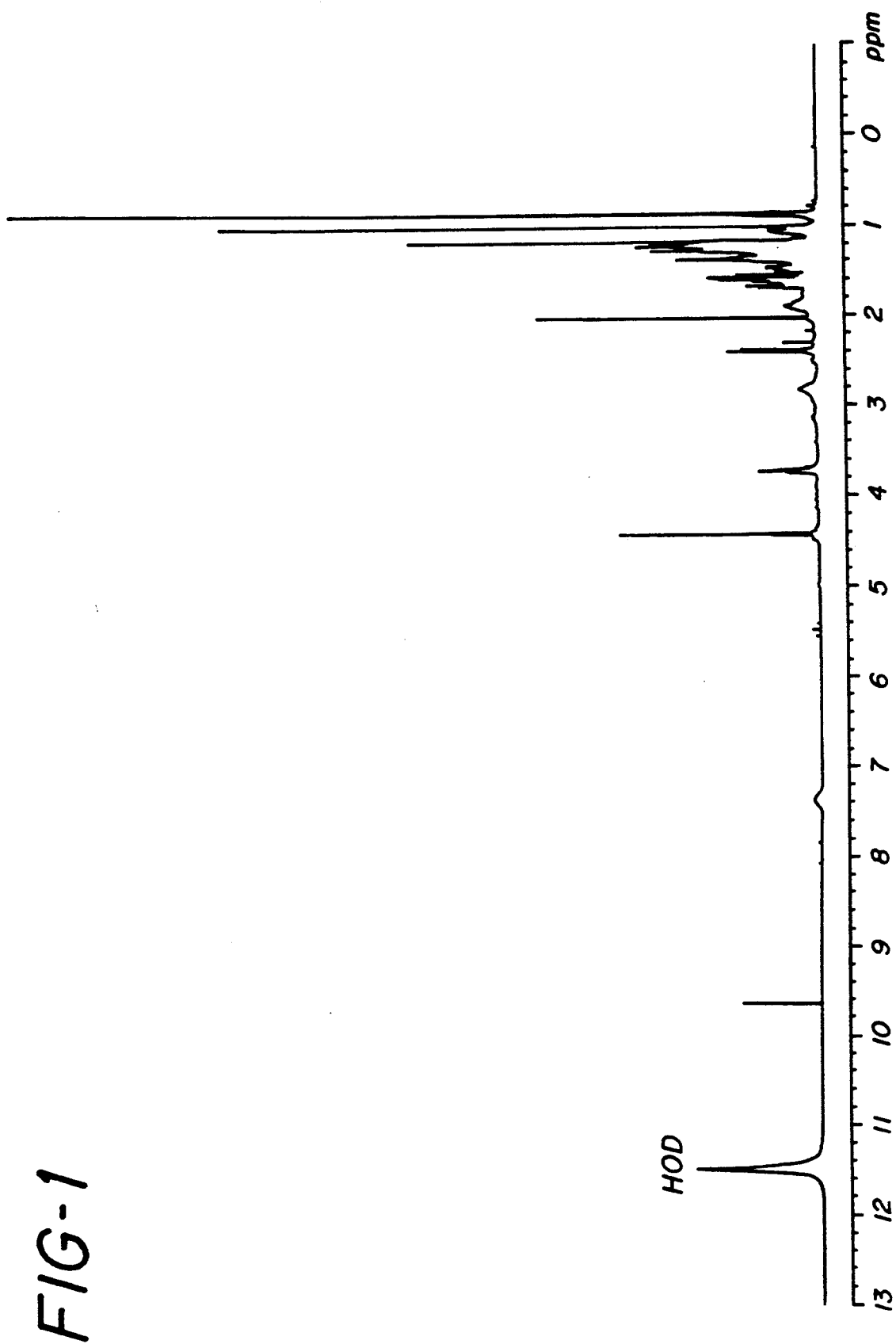
FIG. 1 is a proton nuclear magnetic resonance spectrum for Compound IA.

The compound are light-colored solids characterized by the following spectral properties.

ULTRAVIOLET SPECTRAL DATA of Compound IA:

At 25 μg/ml in MeOH $\lambda_{max}$:275 nm ($\epsilon$=13,100)

At 25 μg/ml in MeOH+20 μl 1.0N NaOH $\lambda_{max}$:207 nm, 287 nm ($\epsilon$=17,300), 306 nm ($\epsilon$=19,000)

At 25 μg/ml in MeOH+20 μl 1.0N HCl $\lambda_{max}$:276 nm ($\lambda$=17,300)

INFRARED SPECTRAL DATA of Compound IA: 2929, 1723 (C=O), 1666 (C=O), 1630 (C=O), 1460, 1398, 1176, 1037 cm$^{-1}$.

MASS SPECTRAL DATA p Mass spectra were recorded on a Finnigan MAT 212 instrument in the electron impact (EI) mode at 90 eV. Exact mass measurements were performed at high resolution (HR-EI) using perfluorokerosene (PFK) as internal standard.

Compound IA has the molecular weight 408 (Calcd. for $C_{23}H_{36}O_6$ 408.2512; found 408.2515).

Compound IB (R=COCH$_3$, F$^1$=H) has the molecular weight 534 (Calcd. for $C_{29}H_{42}O_9$ 534.2829; found 534.2832).

Compound IC (R and R$^1$=COCH$_3$) has the molecular weight 576 (Calcd. for $C_{31}H_{44}O_{10}$ 576.2935; found 576.2946).

NMR SPECTRAL DATA $^{13}$C NMR Spectra

The $^{13}$C NMR spectra of Compound IA as well as IB and IC were recorded in CD$_2$Cl$_2$ at 125 MHz on a Varian Unity 500 NMR spectrometer at ambient and low temperature. Because of exchange-broadening processes at ambient temperature, several resonances in Compound IA were not observed. Similarly two were missing in the triacetate (Compound IB) whereas all were observed in the tetraacetate (Compound IC) with broadening exhibited by some resonances (indicated below by asterisk). At −50° C., Compound IA displayed multiple equilibria including one predominant conformer having 23 resonances. The solution spectra of the triacetate (Compound IB) and tetraacetate (Compound IC) at 25° C., showed only two conformer populations in the ratio of ca 7:5 and 3:1, respectively.

Resonances of major and minor conformers (latter in parentheses) are listed. Chemical shifts are given in ppm relative to tetramethylsilane (TMS) at zero ppm using the solvent peak at 53.8 ppm as internal standard.

$^{13}$C NMR Chemical Shifts of Compound IA (CD$_2$Cl$_2$; 23° C.; one apparent conformer): 14.2, 17.3, 17.7, 23.0, 28.4, 29.4, 32.2, 34.2, 35.7, 37.2, 44.8, 53.4, 68.0, 71.0, 102.2, 145.0, 194.1 ppm.

Only 17 out of 23 carbons are observed. The other 6 are exchange-broadened. $^{13}$C NMR Chemical Shifts of Compound IA (CD$_2$Cl$_2$; −50° C.; multiple equilibria; one predominant conformer): 13.0, 14.0, 16.6, 17.4, 22.7, 27.8, 29.0, 31.8, 33.3, 33.7, 34.7, 36.2, 43.7, 47.4, 53.2, 67.3, 70.0, 101.6, 139.6, 144.5, 166.4, 193.6, 207.6 ppm. The carbon count of 23 is in agreement with the molecular formula $C_{23}H_{36}O_6$ derived by HRMS.

$^{13}$C NMR Chemical Shifts of Compound IB (Triacetate) (CD$_2$Cl$_2$; −25° C.; ca 7:5 conformer mixture): 13.3 (14.2), 14.02 (14.06), 17.34 (17.38), 18.9 (18.5), 20.3 (20.3), 20.7 (20.7) (2x), 22.71 (22.68), 28.2 (27.9), 28.98 (28.92), 31.6 (31.6), 32.3 (32.1), 33.2 (32.8), 34.4 (34.3), 35.9 (35.4), 39.1 (39.8), 48.78 (48.63), 56.05 (56.23), 67.3 (66.8), 70.85 (71.1), 109.89 (110.08), 143.9 (143.5), 148.43 (148.50), 155.87 (154.8), 167.16 (167.22), 168.9 (168.4), 170.14 (170.11), 189.8 (191.0), 198.08 (198.03) ppm. All 29 carbons of a major and minor conformer (in parenthesis) are observed in agreement with the molecular formula $C_{29}H_{42}O_9$.

$^{13}$C NMR Chemical Shifts of Compound IC (Tetraacetate) (CD$_2$Cl$_2$; 25° C.; one apparent conformer): 13.8*, 14.1, 17.4, 19.3*, 20.4, 20.7, 20.80, 20.84*, 22.9, 28.6*, 29.4*, 32.0, 33.3, 34.2*, 35.2, 36.5*, 41.2*, 47.9*, 56.4*, 69.7*, 70.8*, 110.5, ~144.6*, 149.2, ~155.5*, 167.4, 168.6, 170.1, 170.2*, 187.3, 198.0 ppm. All 31 carbons are observed in agreement with the molecular formula $C_{31}H_{44}O_{10}$.

$^{13}$C NMR Chemical Shifts of Compound IC (Tetraacetate) (CD$_2$Cl$_2$; −25° C.; ca 3:1 conformer mixture): 13.4 (14.3), 14.02 (14.06), 17.05 (17.16), 18.9 (18.6), 20.22 20.26), 20.66 (20.66), 20.69 (20.69), 20.71 (20.9), 22.70 (22.73), 28.2 (27.9), 29.1 (29.0), 31.6 (31.6), 32.66 (32.68), 33.6 (33.1), 34.6 (34.4)m 36.1 (35.6), 40.4 (40.8), 47.3 (46.8), 55.8 (56.2), 69.2 (68.1), 70.1 (70.5), 109.6 (109.8), 143.9 (143.5), 148.66 (148.64), 155.3 (154.3), 167.15 (167.13), 168.4 (168.3), 169.94 (169.86), 170.2 (169.93), 187.17 (187.14), 197.83 (197.78) ppm. All 31 carbons of a major and minor conformer (in parenthesis) are observed. *broad to very broad signals.

$^1$H NMR Spectra

Figure 2:
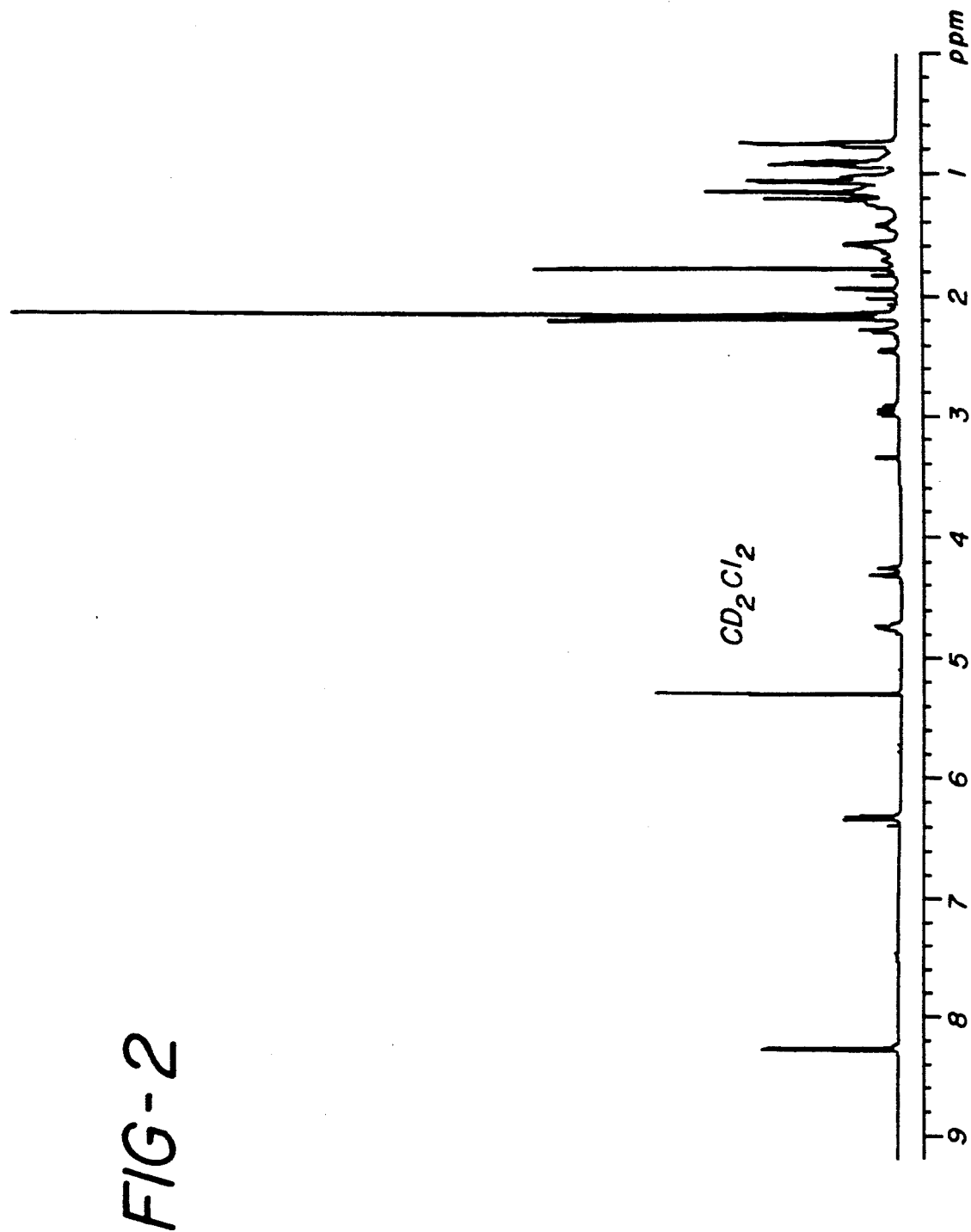
FIG. 2 is a proton nuclear magnetic resonance spectrum for Compound IB.
Figure 3:
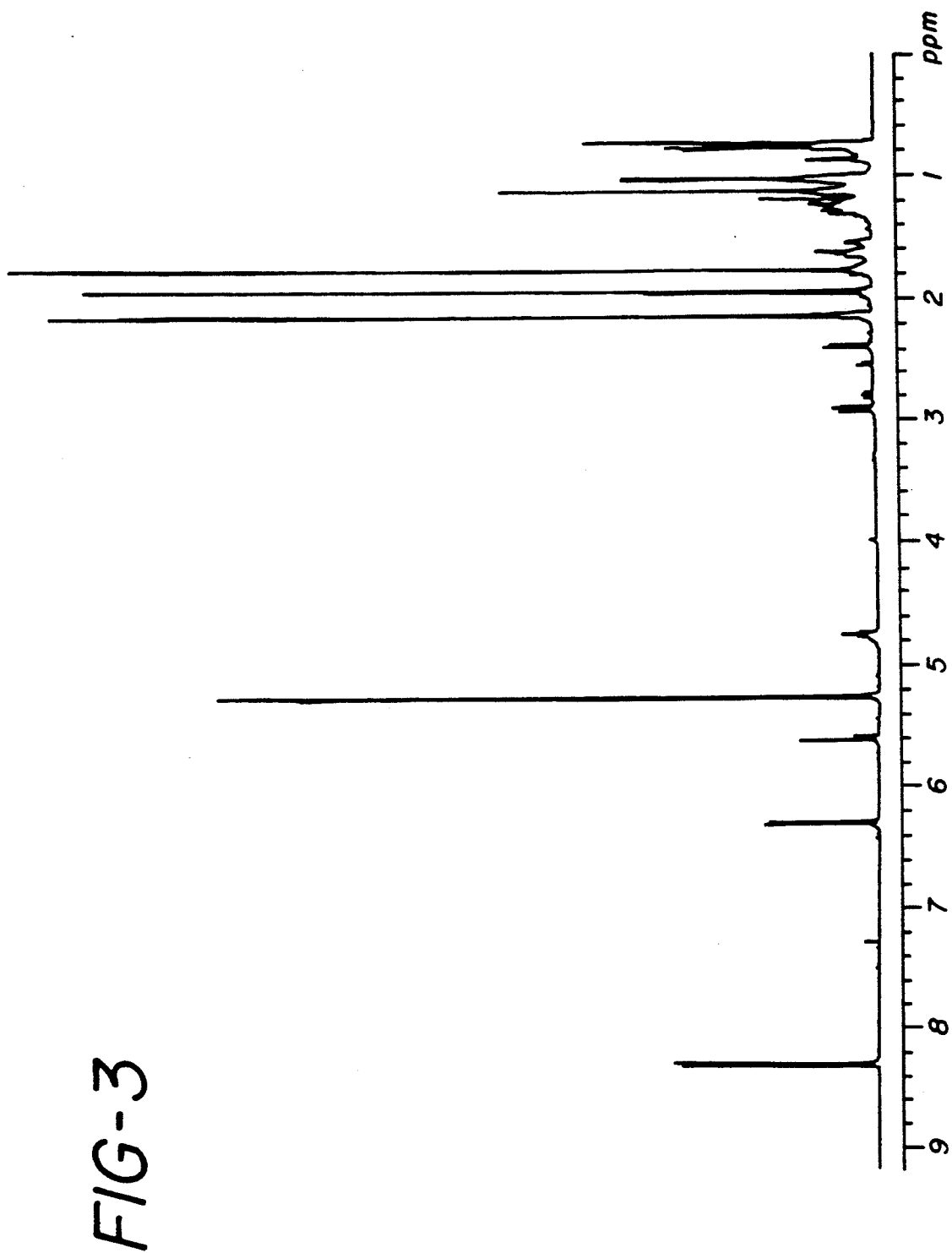
FIG. 3 is a proton nuclear magnetic resonance spectrum for Compound IC.

The $^1$H NMR spectra of Compounds IA, IB and IC are seen in FIGS. 1, 2 and 3. The acetate spectra were recorded at 500 MHz in CD$_2$Cl$_2$ on a Varian Unity 500 NMR spectrometer at −25° C. The spectrum of Compound IA was recorded in CD$_3$COOD at 25° C. Chemical shifts are shown in ppm relative to TMS at zero ppm using the solvent peaks at δ5.32 (CD$_2$Cl$_2$) and δ2.03 (CD$_3$COOD) as internal standards.

The compound produced by the microorganism, Sporormiella australis has antifungal properties against both filamentous fungi and yeasts. It is particularly useful against organisms causing pathogenic mycotic infections such as Candida albicans, Candida guilliermondii, Candida parapsilosis, Cryptococcus neoformans, Candida pseudotropicalis, Candida tropicalis, Saccharomyces cerevisiae, Aspergillus flavus, Aspergillus fumigatus and the like. The properties may be effectively utilized by administering compositions containing an antifungal amount of compound IA, to an area, object or subject, on or in which fungi are to be controlled.

The production of Compound IA may be carried out by cultivating S. australis ATCC 74157 in a suitable nutrient medium under conditions hereinafter described until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate Compound I-A from the other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 per cent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included is a representative seed medium.

TABLE 1

KF SEED MEDIUM

| Component | per liter | Trace Element Mix | per liter |
|---|---|---|---|
| Corn Steep Liquor | 5 g | FeSO$_4$.7H$_2$O | 1 g |
| Tomato Paste | 40 g | MnSO$_4$.4H$_2$O | 1 g |
| Oat Flour | 10 g | CuCl$_2$.2H$_2$O | 25 mg |
| Glucose | 10 g | CaCl$_2$ | 100 mg |
| Trace Element Mix | 10 ml | H$_3$BO$_3$ | 56 mg |
| | | (NH$_4$)$_6$Mo$_7$O$_{24}$.4H$_2$O | 19 mg |
| pH = 6.8 | | ZnSO$_4$.7H$_2$O | 200 mg |

TABLE 2

SOLID FERMENTATION MEDIUM
Production Medium F1

| Component | Amount (per 250-ml flask) |
|---|---|
| Cracked Corn | 10.0 g |
| Ardamine PH | 2.0 mg |
| KH$_2$PO$_4$ | 1.0 mg |
| MgSO$_4$.7H$_2$O | 1.0 mg |
| Na Tartrate | 1.0 mg |
| FeSO$_4$.7H$_2$O | 0.1 mg |

TABLE 2-continued

SOLID FERMENTATION MEDIUM
Production Medium F1

| Component | Amount (per 250-ml flask) |
|---|---|
| ZnSO$_4$.7H$_2$O | 0.1 mg |
| Distilled Water | 10.0 ml |
| no pH adjustment | |

TABLE 3

LIQUID MEDIUM
Medium MOF

| Component | Amount (per liter) |
|---|---|
| D-Mannitol | 75.0 g |
| Oat Flour | 15.0 g |
| Fidco Yeast Extract | 5.0 g |
| L-Glutamic Acid | 4.0 g |
| MES* | 16.2 g |
| Distilled Water | 1000 ml |
| pH adjusted to 6.0 with NaOH | |

*[2-(N-morpholino)ethanesulfonic acid] monohydrate (MES)

TABLE 4

LIQUID MEDIUM
Medium RG122

| Component | Amount (per liter) |
|---|---|
| D-Mannitol | 91.0 g |
| Corn Steep Liquor | 4.0 ml |
| Lard Water | 4.0 g |
| Pectin | 10.0 g |
| KH$_2$PO$_4$ | 4.0 g |
| Tomato Paste | 4.0 g |
| Serine | 10.0 g |
| Peptonized Milk | 4.0 g |
| Peanut Meal | 4.0 g |
| Distilled Water | 1000 ml |
| pH adjusted to 7.0 with NaOH | |

TABLE 5

LIQUID MEDIUM
Medium KRC

| Component | Amount (per liter) |
|---|---|
| Dextrin (starch) | 40.0 g |
| Distiller Solubles | 7.0 g |
| Yeast Extract | 5.0 g |
| CoCl$_2$.6H$_2$O | 50.0 mg |
| Beta Cyclodextrin | 10.0 g |
| Distilled Water | 1000 ml |
| pH adjusted to 7.3 with NaOH | |

Of the foregoing media, the all-liquid medium, Medium MOF, was found to give the best yield of Compound IA.

Generally, in cultivating Sporormiella australis to produce Compound IA, the culture is first grown in a seed medium and the culture growth then used to inoculate a production medium. The production medium may be a solid medium or a liquid medium.

In carrying out the production of Compound IA, frozen mycelia of culture S. australis MF 5672, ATCC 74157 is inoculated into nutrient seed medium at a pH in the range of 5 to 8, preferably pH 7, such as that in Table 1 (KF Seed Medium). The seed flasks are then incubated with agitation at temperatures in the range of from about 15° C. to about 30° C., preferably about 25° C., for a period of from about 2 to 15 days, preferably 3 to 5 days at about 50% relative humidity. When the growth is abundant, usually between 3 to 5 days, the growth may be used to inoculate the production medium for the production of Compound IA.

If appropriate, a second stage fermentation may be carried out in the seed medium for greater production of mycelial mass by inoculating fresh seed medium with a portion of the culture growth and then incubating under similar conditions but for a shortened period. The resulting growth then may be employed to inoculate the production medium which may be solid but is preferably liquid.

When the production is carried out on solid medium, a portion of the seed is used to inoculate the solid medium in a conventional manner and the resulting medium incubated under static conditions preferably at 25° C. and 50 percent relative humidity for 7 to 25 days, preferably 11 to 14 days.

After completion of the cultivation period, as can be determined by HPLC or TLC of the fermentation broth, the product is recovered and thereafter isolated. The secondary metabolites may be extracted from the mycelial growth by shaking at 220 rpm for one hour at 25° C. with either 50 percent aqueous methanol, methanol, ethyl acetate, methyl ethyl ketone or butanol acidified with 0.2 percent trifluoroacetic acid. The mixture is then filtered to remove the solid and to obtain the product in the filtrate. The filtrate is concentrated under reduced pressure to obtain the crude product as residue.

When the fermentation is carried out in a liquid medium, a portion of the seed is used to inoculate the liquid medium in a conventional manner and the resulting medium incubated with agitation, preferably at 25° C. and 50% relative humidity for from 4 to 25 days, preferably 11 to 14 days.

The fermentation broth is acidified to pH 3.0 with sulfuric acid, then an equal volume of ethyl acetate or methyl ethyl ketone is added and the resulting mixture shaken at 220 rpm for 1 hour at 25° C. The broth is then filtered to recover the mycelium. The cells are reextracted several more times, and the extracts combined and the combined extracts subjected to reduced pressure to obtain Compound IA as residue. Other suitable extraction solvents include ethyl acetate, butanol acidified with 0.2 percent trifluoroacetic acid, acetone and methanol.

The product residue from either solid or liquid fermentation is isolated by chromatography, preferably on silica gel, but also may be on silica based reverse phase, dextran gel, and the like.

In carrying out the isolation, the extract is concentrated to obtain an oil containing product which is then partitioned between a non-polar hydrocarbon and polar alcohol to remove non-polar impurities. Preferred solvents for partitioning are hexanes and methanol. The alcohol extract is concentrated to dryness to obtain crude product which may be purified employing silica gel chromatography and using hexane/ethyl acetate/acetic acid as eluant. The appropriate fractions are then pooled, concentrated and further purified. High speed countercurrent chromatography is found to be useful for further purification. In such method, the impure product is dissolved in equal volumes of the upper phase and lower phase of a solvent system consisting of 7 parts hexanes/3 parts ethyl acetate/5 parts methanol/5 parts aqueous 0.025 M $K_2HPO_4$ pH 6.9. The sample is applied to the tail of a multilayer coil which has been completely filled with the lower phase and eluted with the upper phase from the tail to the head of the column at a rotation speed of 800 rpm in the forward direction and collecting fractions. The appropriate fractions are pooled to recover the desired product.

Compounds IB where R is —$COCH_3$ and $R^1$ is H, and Compound IC where both R and $R^1$ are $COCH_3$, may be prepared by the reaction of Compound IA with an appropriate acetylating agent, preferably acetic anhydride. Other acetylating agents such as acetyl halide or activated esters of acetic acid such as 2,4,5-trichlorophenyl ester also may be used. The reaction may be carried out in a solvent such as pyridine. Generally, both the triacetate and tetraacetate are obtained and may be separated by preparative high pressure liquid chromatography.

The acetylation may be carried out by adding acetylating agent to a solution of Compound IA in a solvent such as pyridine and the resulting mixture stirred at room temperature for several hours to obtain a mixture of tri- and tetraacetate of Compound IA. The reaction mixture is concentrated under reduced pressure and the oily residue dissolved in acetonitrile for separation and purification by preparative HPLC. The acetonitrile solution is placed on the column and eluted employing a mobile phase of 0.1 percent $H_3PO_4$ in 60% acetonitrile/40% water. Rate of elution of about 20 ml/min at room temperature with detection at 275 nm has been found to be satisfactory. The appropriate fractions then may be pooled, extracted with methylene chloride, dried, and the dried solution concentrated in vacuo to recover the desired product.

The usefulness of Compound IA as an antifungal agent, especially as an antimycotic agent, may be demonstrated with Compound IA in a broth microdilution assay for the determination of minimum inhibitory concentration (MIC) and minimum fungicidal concentration (MFC) against fungi. In such assay against a panel of fungi selected for their resistance/susceptibility to known compounds, animal virulence, source and clinical importance, Compound IA is found to have very high activity. Compound IA was found to be effective at concentrations of about one-tenth of that required by an established antifungal agent amphotericin B. Against some organisms even greater effectiveness is exhibited.

In the microbroth dilution assay, microorganisms were selected by streaking a yeast culture on Sabouraud dextrose agar (SDA) incubating for 24–48 hours at 35°–37° C., thereafter selecting 3 to 5 characteristic colonies and transferring to a fresh plate and incubating under similar conditions. From the regrowth, 3 to 5 colonies were selected and suspended in 10 milliliters of YM broth (Difco) and incubated for 4 hours at 35°–37° C. shaking at 225 rpm. The 4 hour broth cultures were adjusted optically to 86% transmission resulting in a concentration of 1–5 × $10^6$ cfu/ml which was further diluted 1:100 in YNBD (yeast nitrogen base with 1% dextrose) to obtain a concentration of 1–5 × $10^4$ cfu/ml for use as inocula.

The test compound, Compound IA, and control compounds were prepared as stock solutions of 512 $\mu$g/ml in 10% DMSO and 75 $\mu$l of said solution delivered to each well in column 1 of a 96-well, U-bottomed microtiter plate. The compounds in column 1 were then serially diluted two-fold to yield concentrations from 128 $\mu$g/ml to 0.06 $\mu$g/ml.

The plates containing the diluted compounds were then inoculated with 75 $\mu$l/well of the appropriate microorganism and incubated for 48 hours at 35°–37° C.

with MIC (minimum inhibitory concentration) checks carried out after 24 hours of incubation. Growth and sterility controls for each organism and sterility checks for the compounds also were carried out.

After recording MICs at 24 hours, the microtiter plates are shaken gently to resuspend the cells. A 1.5 μL sample then is transferred from each well of the 96-well microtiter plate to a single reservoir inoculum plate containing SDA. The inoculated SDA and corresponding microtiter plates are incubated for 24 hours at 35°–37° C. For *Cryptococcus neoformans,* SDA plates are inoculated at 48 hours after recording MICs and incubated for 48 hours before reading the MFC. MFC is the lowest concentration of compound at which either no growth or growth of ≦4 colonies occur.

| Minimum Fungicidal Concentration (MFC) (μg/ml) | | |
|---|---|---|
| Pathogen | Compound IA | Control* |
| C. albicans (MY1028) | 0.063 | 0.5 |
| C. albicans (MY1055) | 0.031 | 0.5 |
| C. albicans (MY1750) | 0.125 | 1 |
| C. guillermondii (MY1019) | <0.015 | 1 |
| C. parapsilosis (MY1010) | 0.125 | 1 |
| C. pseudotropicalis (MY2099) | <0.015 | 2 |
| C. tropicalis (MY1012) | <1.015 | 4 |
| C. neoformans (MY1051) | 0.031 | 1 |
| C. neoformans (MY1146) | 0.125 | 1 |
| C. neoformans (MY2061) | 0.015 | 1 |
| S. cerevisiae (MY1976) | <0.015 | 1 |

*Amphotericin B

The compound produced by the microorganism is also useful for inhibiting the growth of filamentous fungi. Such use may be illustrated in the following test with *Aspergillus niger, Aspergillus flavus, Aspergillus fumigatus, Fusarium oxysporum, Rhizomucor miehei, Ustilego zeae* and the like.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

The samples to be tested for production of antifungal agent are applied to 6.2 mm. filter paper discs (25 microliter/disc) and air dried at 24° C. When the sample to be tested is crude broth, it may be centrifuged prior to application. The discs bearing the material to be tested are then applied employing sterile conditions to the seeded assay plates and the samples rewet with 25 percent sterile aqueous dimethylsulfoxide (25 μl/disc). The assay plates are then incubated at either 28√ C. or 37° C. for 24 hours. Following incubation, the inhibition zones are measured. Growths are also noted as to appearance. Compound IA is seen to effectively inhibit growth of the fungal organisms.

The compounds also have antimicrobial activity against bacteria. Thus, is an assay carried out in a manner similar to that above described for filamentous fungi, zones of inhibition are noted when *Bacillus subtilis* is a test organism.

The following further illustrates the invention but are not to be construed as limiting:

Use of *Sporormiella australis* to Produce Compound IA

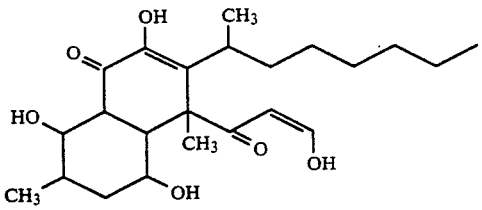

A frozen vegetative mycelia or *Sporormiella australis* MF 5672 in the culture collection of Merck & Co., in Rahway, N.J. was inoculated into 54 milliliters of KF seed medium (Table 1) in a 250 milliliter unbaffled Erlenmeyer flask. The seed flasks were incubated for three days at 25° C. and 50 percent relative humidity on a rotary shaker with a 5-cm throw at 220 rpm.

Two milliliter portions of the 3-day culture growth were used to inoculate fermentation production medium, Medium MOF, contained in eighty 250 milliliter flasks and the inoculated media incubated under static conditions at 25° C. and 50 percent relative humidity for 11 days.

After 11 days, 50 milliliters of ethyl acetate was added to each flask and the mixture agitated at 220 rpm for 2 hours at room temperature and thereafter filtered through a celite pad to obtain 25.3 grams of ethyl acetate extract.

The extract was concentrated under reduced pressure to an oil which was then partitioned between 650 milliliters of hexanes solvent and 200 milliliters of methanol. The methanol layer was concentrated to dryness in vacuo to obtain 3.54 grams of crude antibiotic compound (Compound IA) which dissolved to a final volume of 17.7 milliliters in hexane/ethyl acetate containing 1 percent acetic acid. A 15.3 milliliter portion (3.04 grams of Compound IA) was applied to a 377 gram silica gel 60 (0.040–0.063 mm, 230–400 mesh, E. Merck) column, 5 cm×45 cm, which had been equilibrated with hexane/ethyl acetate (3:2) containing 1 percent acetic acid. The column was eluted with the same solution at 15 ml/min and 24 milliliter fractions collected. The product rich fractions were determined by analytical HPLC (Phenomenex Ultracarb 5 ODS 30, 15 cm×4.6 mm, eluted with a mobile phase consisting of 55% acetonitrile/45% aqueous 0.025 M K₂HOP₄ adjusted to pH 6.9 with conc. H₃PO₄, flow rate 1 ml/min at 55° C., detection at 275 nm).

The crude fraction pool was concentrated in vacuo to 410 milligrams of yellow oil which was then dissolved in 10 milliliters of ethyl acetate. A 3-milliliter portion of this solution was concentrated to dryness and further purified by high speed countercurrent chromatography (using a Countercurrent Chromatograph obtained from P.C. Inc., 11805 Kim Place, Potomac Maryland, USA). The sample was dissolved in 2 milliliters of the upper phase and 2 milliliters of the lower phase of a solvent system consisting of 7 parts hexans/3 parts ethyl acetate/5 parts methanol/5 parts aqueous 0.025 M K₂HPO₄ pH 6.9. The sample was applied to the tail of a #14 analytical multilayer coil (P.C. Inc.) which had been filled completely with the lower phase of the above solvent system. The coil was then eluted with the upper phase of the solvent system at 3 ml/min from the tail to the head of the column, at a rotation speed of 800 rpm in the forward direction collecting 7.5 milliliter fractions. From fractions 53–64 purified, Compound IA amounting to 41 milligrams was obtained.

The Compound IA had the spectral properties previously described.

Compound IA had the following elemental analysis: Calc. for $C_{23}H_{36}O_6$ 67.65%, C, 8.82%, H, 0% N. Found 67.31%, C, 8.24%, H, <0.02% N, Preparation of Derivatives of Compound IA Triacetate (IB) and Tetraacetate (IC) of Compound IA

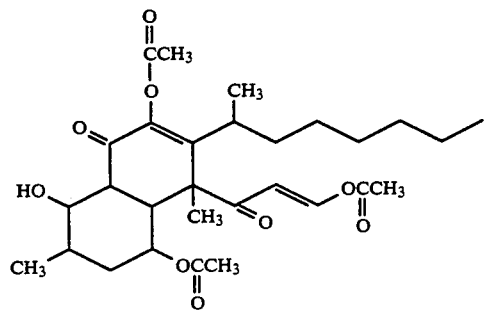

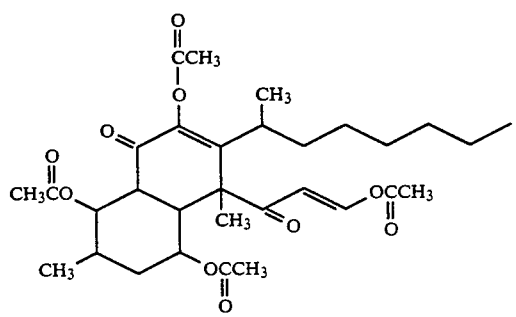

20.4 milligrams of Compound IA was dissolved in 0.5 milliliter of pyridine, and to it was added 0.5 milliliter of acetic anhydride and the resulting mixture was stirred at room temperature for 3.75 hours to obtain acetate products. The reaction mixture was then concentrated to dryness in vacuo. The resulting residue was dissolved in 5 milliliters of acetonitrile and the solution concentrated under reduced pressure. The resulting mixture was dissolved in 1 milliliter of acetonitrile and placed on a preparative HPLC column (Whatman Partisil 10 ODS, 22 mm×25 cm) and eluted employing a mobile phase of 60% acetonitrile containing 0.1% $H_3PO_4$/40% water at 20 ml/min at room temperature with detection at 275 nm to separate the products. Eight milliliter fractions were collected. Fractions 26 to 29 which were found to contain the triacetate were pooled and the pooled fractions extracted with 32 milliliters of methylene chloride. The methylene chloride solution was dried over anhydrous sodium sulfate and the dried solution concentrated to dryness in vacuo to obtain 8 milligrams of the triacetate (Compound IB). Fractions 33 to 36 which were found to contain the tetraacetate were similarly treated to obtain 11 milligrams of the tetraacetate (Compound IC).

what is claimed is

1. A biologically pure culture of *Sporormiella australis* ATCC 74157.

2. A biologically pure culture of *Sporormiella australis* ATCC 74157 which is capable of producing a compound represented by the formula:

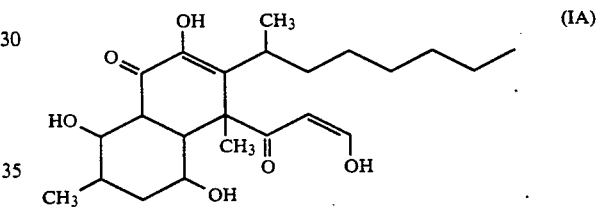

(IA)

* * * * *